(12) United States Patent
Kurtiak

(10) Patent No.: US 9,901,494 B2
(45) Date of Patent: Feb. 27, 2018

(54) DISPOSABLE DIAPER WITH CHANGING ACCESSORIES ENCLOSURE

(71) Applicant: Neil Adam Kurtiak, Beaufort, SC (US)

(72) Inventor: Neil Adam Kurtiak, Beaufort, SC (US)

( * ) Notice: Subject to any disclaimer, the term of this patent is extended or adjusted under 35 U.S.C. 154(b) by 152 days.

(21) Appl. No.: 14/029,754

(22) Filed: Sep. 17, 2013

(65) Prior Publication Data

US 2015/0080835 A1     Mar. 19, 2015

(51) Int. Cl.
*A61F 13/551*     (2006.01)

(52) U.S. Cl.
CPC ...... *A61F 13/5519* (2013.01); *A61F 13/5512* (2013.01); *A61F 2013/55125* (2013.01)

(58) Field of Classification Search
CPC .. A61F 2013/55125; A61F 2013/55155; A61F 2013/55195; A61F 13/84; A61F 2013/8402; A61F 2013/49098; A61F 13/51498

USPC ...................... 604/385.06; 206/494
See application file for complete search history.

(56) References Cited

U.S. PATENT DOCUMENTS

| 2004/0092901 | A1* | 5/2004 | Reece et al. | 604/385.06 |
| 2005/0261654 | A1* | 11/2005 | Swanson | 604/385.06 |
| 2007/0032769 | A1* | 2/2007 | Cohen | A61F 13/8405 |
| | | | | 604/385.06 |

* cited by examiner

*Primary Examiner* — Peter S Vasat
(74) *Attorney, Agent, or Firm* — Oakwood Law Group, LLP; Stephen Liu

(57) ABSTRACT

A disposable diaper with concealed baby wipes enclosure ensures that absorbent baby wipes are readily available when the diaper needs to be changed. The diaper is made to contain plurality of baby wipes or other foldable, not bulky diaper changing accessories. The concealed compartment is made accessible by pulling on a tab that tears the enclosure open.

5 Claims, 5 Drawing Sheets

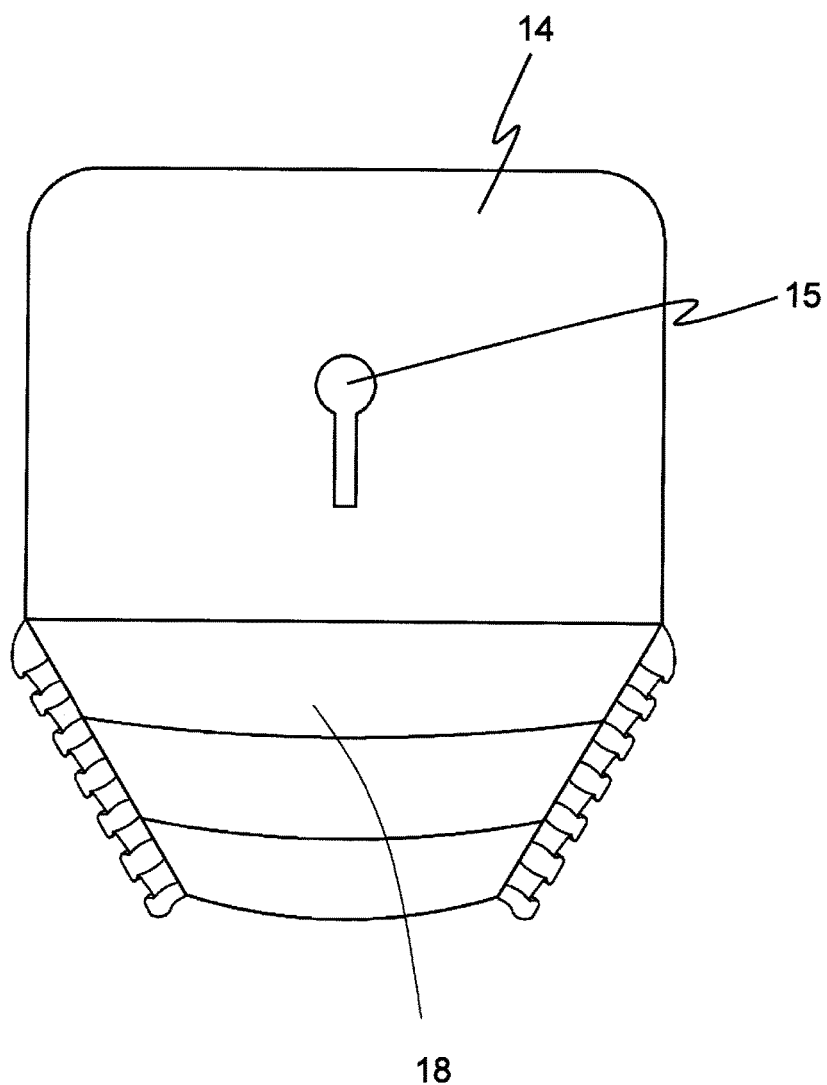

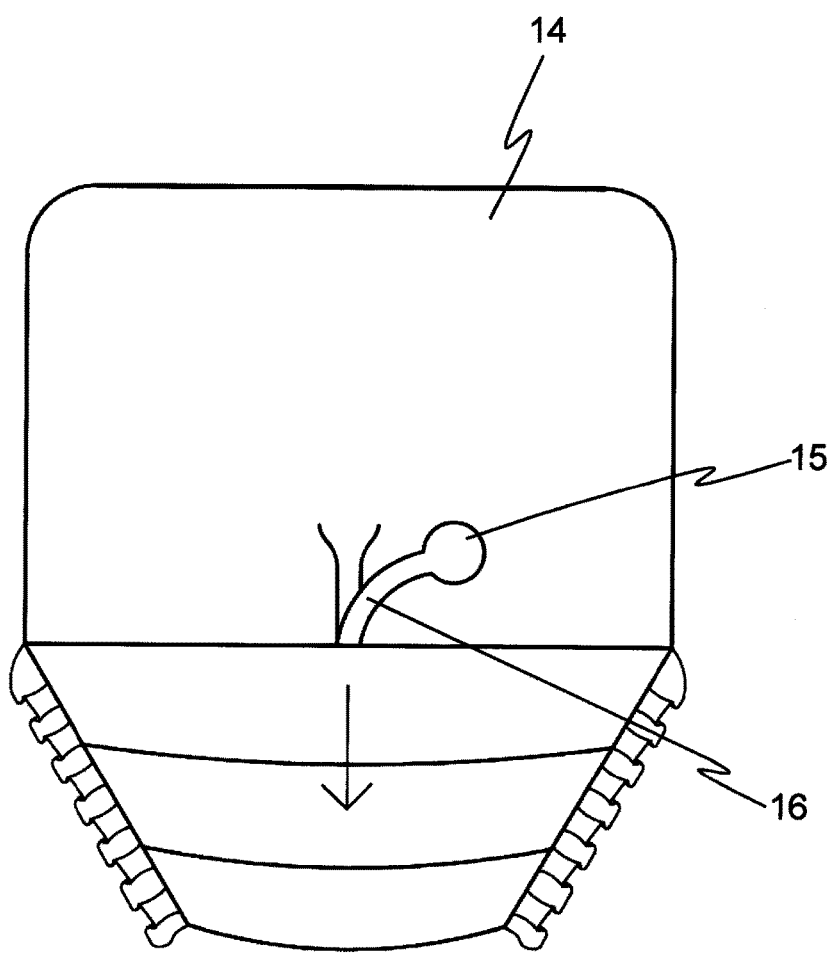

DISPOSABLE DIAPER WITH CHANGING ACCESSORIES ENCLOSURE

REFERENCE TO RELATED APPLICATIONS n/a

BACKGROUND OF THE INVENTION

Field of the Invention

The present invention relates to a field of disposable diapers, more particularly to disposable diapers equipped with supplemental diaper changing accessories.

Description of Related Art

Invention of disposable diapers freed a lot of time involved in changing, laundering and ironing of diapers spent on these tasks before the invention. It eased caretaking for babies and allowed young parents and baby sitters to travel with babies while carrying with them fewer diaper changing accessories. Still, baby caretakers usually need a diaper bag that not only contains diapers but also a separate box with baby wipes and some additional accessories. To accommodate all this diaper bags are rather sizable and cumbersome to carry around. Therefore, a need arose for a disposable diaper that provides a set of diaper changing accessories, cleaning baby wipes in particular, so that a person taking care of the baby could have most changing accessories in one packet which can be readily placed in a purse or regular handbag.

Some means for providing diaper changing accessories attached to disposable diapers are known in the prior art. More specifically, by way of example, U.S. Patent Application Publication No. 2005/0203476 A1 to Stegall discloses a diaper with a pouch or plastic pocket that holds items such as baby wipes and powder, and diaper rash ointment. The pocket is secured in the diaper and is sealed with a zipper type closure.

U.S. Pat. No. 5,582,605 to Lepie teaches the concept of a disposable diaper adapted to carry toiletries and other accessories. The diaper accommodates an array of compartments located on the front panel of the diaper beneath the belt area of the diaper. Each compartment is equipped with a closure structure and contains items such as cleaning towels, baby powder and a trash bag.

U.S. Patent Application Publication No. 2006/0020252 to Strong discloses a self-contained disposable assembly that has a compartment with a disposable bag inside attached to the diaper. The diaper containment compartment is sealed with a re-sealable type of closure.

U.S. Pat. No. 4,738,678 to Paulis teaches a concept of a diaper and wipe combination where the wipe becomes accessible once a clean diaper is unfolded.

The disclosures propose several solutions to combinations of a diaper and changing accessories but they make diapers bulky, provide pouches that a baby can accidentally open or fall short in the convenience area. Therefore a need still exists for a diaper that contains accessories in a way that does not add much volume to the diaper, that avoids the danger of the baby accidentally opening accessory compartments, that is easy to use and provides quick and easy access to the toiletries, and that can provide the necessities needed for changing a baby when needed while being easily carried in a regular purse before use.

SUMMARY OF THE INVENTION

In an exemplary embodiment of the present invention, there is disclosed a disposable diaper equipped with changing accessories enclosure that can accommodate changing accessories such as absorbent wipes, dirty diaper disposing bag, and other foldable materials. The diaper of the present invention is constructed in a way similar to other disposable diapers except that, in the front panel of the diaper, it has a hidden enclosure that is lined with impermeable layer and can accommodate, for example, a number of absorbent wet wipes. On the back panel of the diaper, there is an easy to grasp colored pull tab that is attached to a tape or string concealed under the outer layer of the diaper. The string runs across the crotch area to the front panel and to the hidden enclosure of the diaper. While enclosure is not accessible when a new diaper is first fastened onto a person it is made accessible by pulling on the colored tab ripping open the outer layer of the diaper all the way to the front and to the hidden enclosure containing changing accessories, much like a cigarette packet is opened.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

BRIEF DESCRIPTION OF THE DRAWINGS

Other aspects, features, and advantages of the present invention will become more fully apparent from the following detailed description, the appended claims, and the accompanying drawings in which similar elements are given similar reference numerals.

FIG. 2 is a back view of the diaper.

FIG. 3A is a back view of the diaper after initial pulling on the pull tab.

DESCRIPTION OF THE PREFERRED EMBODIMENT

Figure 1:
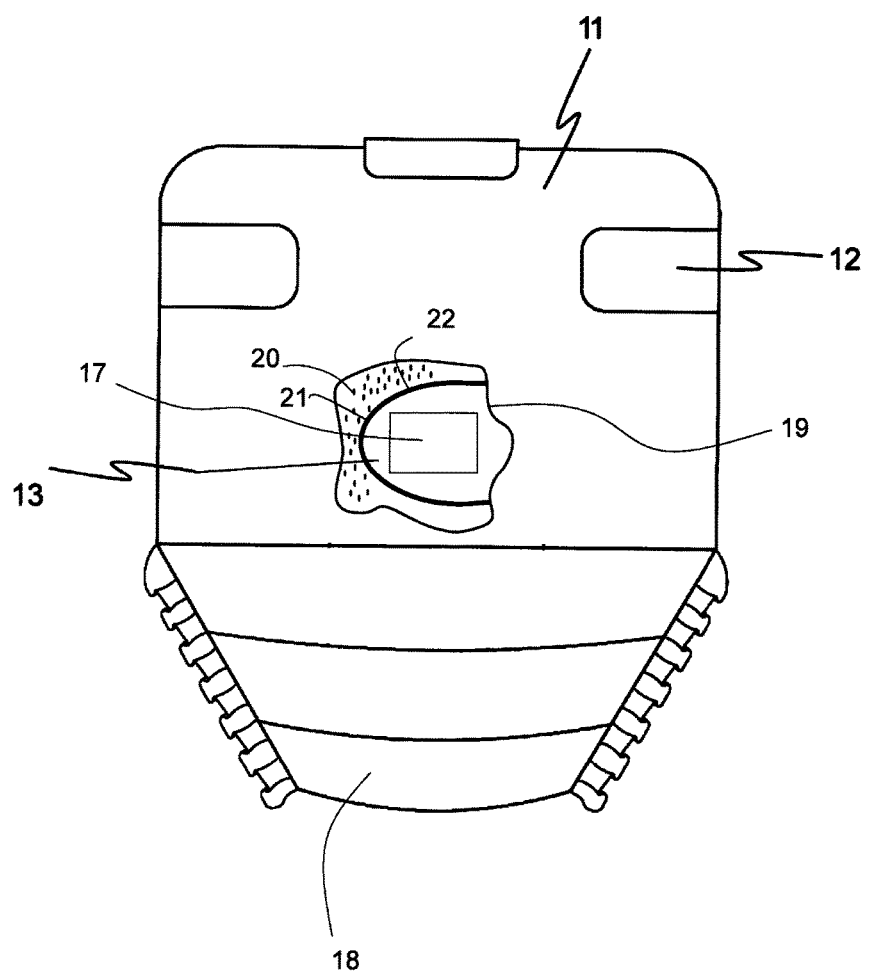
FIG. 1 is a schematic front view of the diaper, with a portion broken away showing the changing accessories enclosure stored within the front panel of the diaper.
Figure 3B:
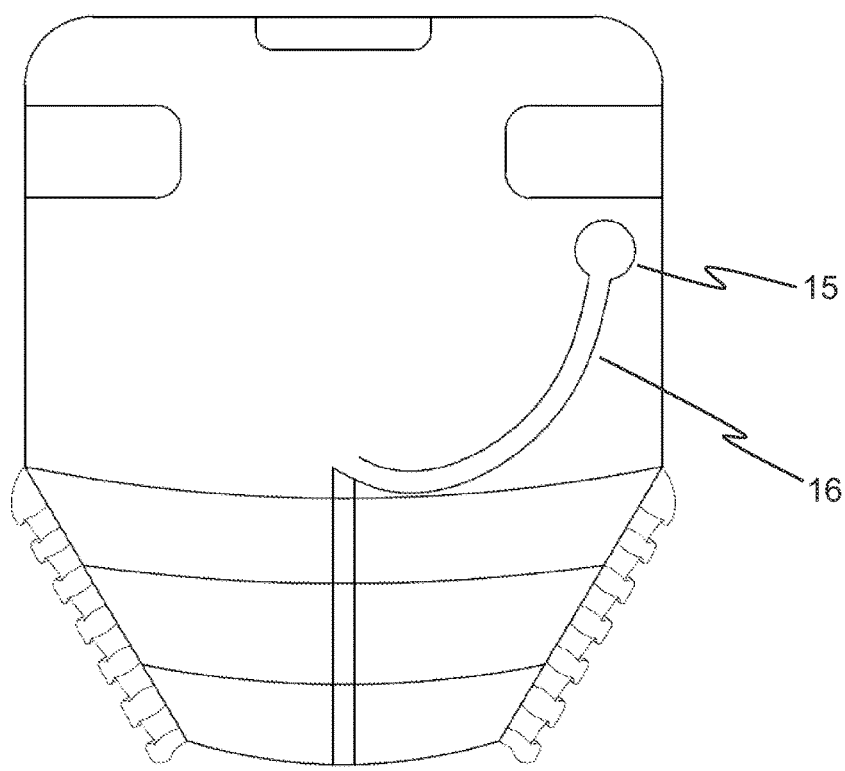
FIG. 3B is a front view of the diaper after pulling the tab all the way to the front.
Figure 3C:
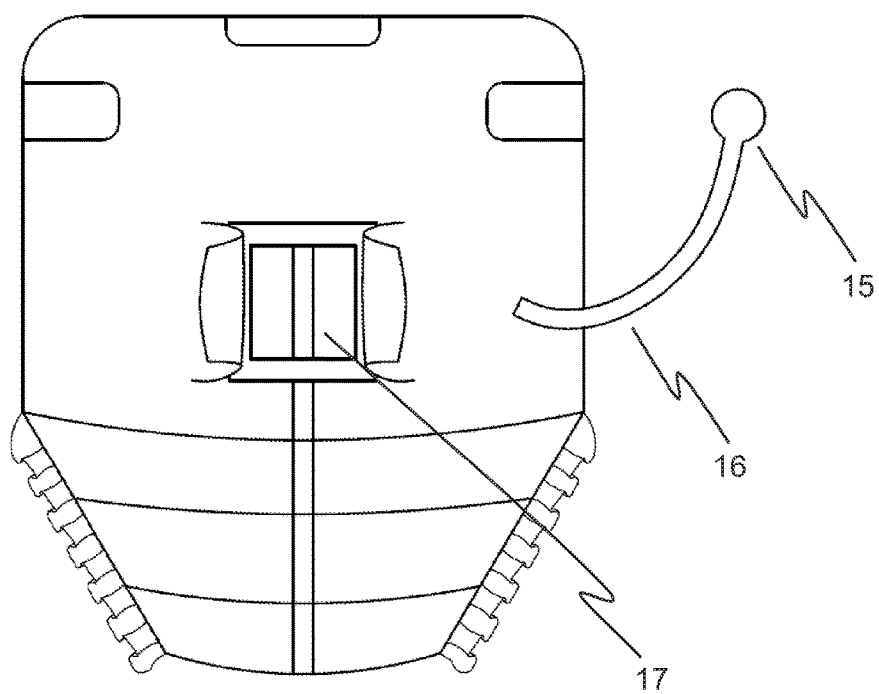
FIG. 3C is a front view of the diaper after pulling the tab all the way up the front panel and tearing the hidden enclosure open.

Referring to FIG. 1, there is disclosed a front view of a disposable diaper, which shows a front panel 11 with fastening strips 12, and a crotch area 18 connected to the lower edge of the front panel. FIG. 1 is a front view of said diaper with a portion broken away showing a hidden changing accessories enclosure 13 stored under the external surface 19 within the front panel of the diaper. Said hidden enclosure 13 is substantially rectangular in shape and lined with impermeable material 21 to isolate its contents both from the inner layers 20 of the diaper as well as its external surface. FIG. 2 shows a back view of said diaper, which shows a back panel 14 of said diaper with a red pull tab 15, and said crotch area 18 connected to the back panel. The color of the pull tab can be different it should, however, differ significantly from the color of said diaper to make it easily discernible. The pull tab 15 is attached to a string or tape (not shown) that, when the diaper is in use, is concealed under the external surface of said diaper. Said string or tape 16 runs from the tab 15 through the crotch area 18 of the diaper to the upper edge 22 of the hidden enclosure 13. When a baby caregiver needs to change the diaper and access baby wipes hidden in the enclosure 13 they pull the red tab 15 tearing the external surface of the diaper from the back to the front ripping the hidden enclosure open as in FIG. 3 A through C. The enclosure 13 accommodates three to four absorbent baby wipes 17 as in FIG. 3C.

More specifically, to use the invention when the baby is ready to be changed, one undresses them and lies down on their back. Next, one lifts the baby's legs up towards their chest revealing the red pull tab, grasps the tab and pulls up towards the crotch area of the diaper tearing its outer layer until it rips open the middle of the concealed enclosure thus providing access to the baby wipes contained therein. Subsequently, one unfastens the diaper revealing the child's bottom and the waste, removes the dirty diaper, cleans the child with the wipes, discards the wipes in the diaper and throws the diaper out in the trash. One can also add a step of putting the dirty diaper in a disposing bag that can be enclosed therein, as well. Finally one puts a new diaper on the child and the child is now ready for the next time to change them.

The diapers are manufactured according to standard manufacturing techniques known in the art using standard materials.

In the preferred embodiment of the invention the hidden enclosure is located in the front panel of the diaper. The tab that serves to open the enclosure is positioned in the back panel to avoid baby accidental pulling on it and ripping the diaper while it is in use. Nonetheless, the scope of the invention does not limit positioning of the hidden enclosure and the pull tab to the locations described herein. It is also well within the scope of the invention to equip the diaper with other accessories, such as, e.g., a diaper disposing bag, that do not add substantially to the bulk of the diaper but make caring for the baby while on the go substantially easier.

The embodiments discussed herein were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are entitled.

What is claimed is:

1. A disposable diaper having hidden changing accessories comprising:
   a diaper having a front panel; a back panel; and a crotch area;
   wherein said crotch area has a upper edge integrally connected to a lower edge of said front panel and has a lower edge integrally connected to said back panel;
   wherein said front panel has a diaper changing accessories enclosure positioned under an external surface of said front panel, said enclosure contains changing accessories and is surrounded with impermeable material to isolate said changing accessories from inner layers of said front panel;
   wherein said back panel has a colored pull tab attached to a connecting member, said member located underneath the external surface of said diaper runs from said pull tab to an upper edge of said accessories enclosure.

2. The disposable diaper having hidden changing accessories of claim 1 wherein said changing accessories comprise absorbent baby wipes.

3. The disposable diaper having hidden changing accessories of claim 1 wherein said changing accessories comprise baby wipes and diaper disposing sac.

4. The disposable diaper having hidden changing accessories of claim 1 wherein said enclosure is revealed and access to the changing accessories is provided once said pull tab together with said connecting member is pulled and said external surface of said diaper is torn apart.

5. A diaper containing hidden changing accessories comprising:
   a disposable diaper having an external surface; inner layers, a changing accessories enclosure concealed therein; and a pull tab attached to a connecting and enclosure-opening member;
   wherein said changing accessories enclosure located under the external surface contains changing accessories inside and is surrounded with impermeable material to isolate said changing accessories from the inner layers of said diaper;
   wherein said member is concealed underneath the external surface of said diaper and runs from said pull tab to substantially an upper edge of said accessories enclosure;
   wherein said enclosure is revealed and access to the changing accessories is provided once said pull tab together with said connecting member is pulled and said external surface of said diaper is torn apart; wherein said diaper forms a front panel and a back panel; wherein said enclosure is located in said front panel and said pull tab is located in said back panel.

* * * * *